(12) United States Patent
List

(10) Patent No.: US 7,842,060 B2
(45) Date of Patent: Nov. 30, 2010

(54) LANCET DEVICE FOR GENERATING A PUNCTURE WOUND, AND LANCET DRIVE ASSEMBLY

(75) Inventor: Hans List, Hesseneck-Kailbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 677 days.

(21) Appl. No.: 11/298,388

(22) Filed: Dec. 9, 2005

(65) Prior Publication Data

US 2006/0155317 A1     Jul. 13, 2006

(30) Foreign Application Priority Data

Dec. 10, 2004    (DE)   ............... 10 2004 059 491

(51) Int. Cl.
*A61B 10/00* (2006.01)
*A61B 5/00* (2006.01)
*A61B 17/14* (2006.01)
*A61B 17/32* (2006.01)

(52) U.S. Cl. ............... 606/182; 606/181; 606/183; 600/562; 600/583; 600/584

(58) Field of Classification Search ......... 606/181–182, 606/583–584, 562
See application file for complete search history.

(56) References Cited

U.S. PATENT DOCUMENTS

| | | | |
|---|---|---|---|
| 4,469,110 A | | 9/1984 | Slama |
| 4,924,879 A | | 5/1990 | O'Brien |
| 5,350,392 A | * | 9/1994 | Purcell et al. ............... 606/182 |
| 6,015,392 A | * | 1/2000 | Douglas et al. ............. 600/583 |
| 6,086,545 A | * | 7/2000 | Roe et al. .................. 600/570 |
| 6,332,871 B1 | * | 12/2001 | Douglas et al. ............. 600/583 |
| 6,409,740 B1 | | 6/2002 | Kuhr et al. |
| 6,419,661 B1 | * | 7/2002 | Kuhr et al. .................. 604/207 |
| 6,464,649 B1 | * | 10/2002 | Duchon et al. .............. 600/583 |
| 6,589,260 B1 | | 7/2003 | Schmelzeisen-Redeker et al. |
| 6,706,000 B2 | * | 3/2004 | Perez et al. ................. 600/583 |
| 6,929,650 B2 | | 8/2005 | Fukuzawa et al. |

(Continued)

FOREIGN PATENT DOCUMENTS

DE     199 09 602 A1    9/2000

(Continued)

*Primary Examiner*—Max Hindenburg
*Assistant Examiner*—Sean P Dougherty
(74) *Attorney, Agent, or Firm*—Bose McKinney & Evans LLP

(57) ABSTRACT

A lancet device for generating a puncture wound in a skin surface, comprising a housing, in which a lancet can be moved on a puncturing path, a lancet drive with a drive rotor that can be driven by a drive spring, a lancet coupling mechanism that transforms a rotational motion of the drive rotor into a puncturing and returning motion of the lancet during a working cycle of the lancet drive, a reference element that is mobile relative to the lancet and relative to the housing and is fixed in a defined position relative to the lancet drive during the puncturing and rests against the surface of the skin with a contact surface thereof such that a puncture wound with a reproducible puncturing depth is generated by the puncturing motion, and a reference element coupling mechanism that is coupled to the lancet drive in order to move the reference element. The invention further relates to a suitable lancet drive assembly for a lancet device of this type.

15 Claims, 10 Drawing Sheets

U.S. PATENT DOCUMENTS

| | | |
|---|---|---|
| 6,969,359 B2 * | 11/2005 | Duchon et al. .............. 600/583 |
| 7,201,723 B2 * | 4/2007 | Chan ......................... 600/583 |
| 2003/0109808 A1 * | 6/2003 | Takinami et al. ............ 600/584 |
| 2003/0191415 A1 * | 10/2003 | Moerman et al. ........... 600/584 |
| 2003/0199744 A1 * | 10/2003 | Buse et al. ................. 600/347 |
| 2004/0343318 | 2/2004 | Fritz et al. |
| 2004/0068283 A1 | 4/2004 | Fukuzawa et al. |
| 2004/0092996 A1 | 5/2004 | List et al. |
| 2004/0215224 A1 * | 10/2004 | Sakata et al. ............... 606/181 |
| 2005/0085839 A1 * | 4/2005 | Allen et al. ................. 606/181 |
| 2007/0060843 A1 * | 3/2007 | Alvarez-Icaza et al. ..... 600/583 |
| 2007/0156065 A1 * | 7/2007 | Chan ......................... 600/583 |
| 2007/0233167 A1 * | 10/2007 | Weiss et al. ................. 606/182 |

FOREIGN PATENT DOCUMENTS

| | | |
|---|---|---|
| DE | 100 26 172 A1 | 11/2001 |
| DE | 10 2004 059 491.0-35 | 7/2006 |
| EP | 1 358 844 A1 | 11/2003 |
| EP | 1 384 438 A1 | 1/2004 |
| WO | WO 02/36010 A1 | 5/2002 |
| WO | WO 2005/096941 A1 | 10/2005 |

\* cited by examiner

LANCET DEVICE FOR GENERATING A PUNCTURE WOUND, AND LANCET DRIVE ASSEMBLY

RELATED APPLICATIONS

This application claims priority to DE 100 2004 059 491.0, filed Dec. 10, 2004.

BACKGROUND

The invention relates to a lancet device for generating a puncture wound, in particular for withdrawing a body liquid for diagnostic purposes, and a lancet drive assembly for a lancet device.

In order to obtain a small quantity of body liquid (blood and/or interstitial liquid) from a part of the body (usually a finger or ear lobe) for analytical-diagnostic purposes, lancets are used that are stuck into the respective body part in order to generate a puncture wound. If this is effected manually, specially trained personnel are required for this purpose. Even then, puncturing is associated with considerable pain.

Blood withdrawal systems consisting of a lancet device and corresponding lancets that are specifically adapted to the corresponding lancet device have been in use for a long time. A housing of the lancet device contains a lancet drive by means of which a lancet is stuck mechanically into the skin. A spring serves as drive element for the puncturing motion. Initially very simple designs were customary, in which the lancet was directly attached to one end of a compression spring that was arranged in an elongated housing (e.g. U.S. Pat. No. 4,469,110).

However, blood withdrawal systems of this type failed to meet the difficult requirements that need to be satisfied when regular monitoring of analytical blood values is required. This applies in particular to diabetics who should control their blood sugar level frequently in order to be able to keep it within certain limits by injecting insulin. Extensive scientific investigations have shown that an intensive therapy scheme involving at least four blood analyses per day can achieve a dramatic reduction of extremely severe secondary damage caused by diabetes mellitus (for example retinopathy resulting in the patient going blind).

A prerequisite of this type of intensive therapy is that the withdrawal of blood be associated with as little pain as possible. A number of different blood withdrawal systems have been developed aiming for improvement in this regard.

Withdrawal of blood with little pain is made possible by lancet devices, whose lancet drive includes a drive rotor onto which acts, on the one hand, the drive spring on one side (drive side) such that the drive rotor can be put into a rotational motion about a rotation axis, and which, on the other hand, is coupled via a coupling mechanism (on the output side) to the lancet such that the rotation of the drive rotor resulting from the relaxation motion of the drive spring is transformed into a puncturing motion. The present invention relates to a lancet device with a rotor lancet drive of this type that is known in various embodiments.

Usually, the output-side coupling mechanism is designed such that the lancet is coupled to the drive rotor during the entire puncturing and returning motion (drive phase of the motion of the lancet drive) and thereby the lancet motion is completely controlled by the corresponding motion of the drive rotor. An early example of a design of this type is shown in U.S. Pat. No. 4,924,879. More modern embodiments are described, for example, in U.S. Pat. Nos. 6,409,740 and 6,419,661.

The known rotor lancet drives are usually tensioned by rotating the rotor backwards, against the force of the drive spring, by means of a suitable "drive side coupling mechanism." More recently, a design has become known, in which an additional tensioning rotor is used for tensioning the drive spring. This allows the tensioning of the lancet drive to proceed in a tensioning phase of its motion by rotating the tensioning rotor in the same direction as the rotation of the drive rotor in the drive phase. This drive principle is also called OWADAC (one way alternating drive and cocking). A rotor drive of this type is described, for example, in EP 1384438 A1.

Despite extensive developmental work, there is still great interest in a lancet device that meets the, to some extent contradictory, requirements (minimal pain sensation, easy operability, compact design, cost-efficient construction) simultaneously and to the extent possible. A further requirement is that there should be no or as little as possible contamination of the lancet device during its use by exiting blood. It is an object of the invention to meet these requirements to the extent possible.

SUMMARY OF THE INVENTION

This object is met by a lancet device for generating a puncture wound in a skin surface, in particular for withdrawing blood for diagnostic purposes, comprising a housing, in which a lancet can be moved on a puncturing path, a lancet drive with a drive rotor that can be driven by a drive spring, a lancet coupling mechanism that transforms a rotational motion of the drive rotor into a puncturing and returning motion of the lancet during a working cycle of the lancet drive, a reference element that is mobile or moveable relative to the lancet and relative to the housing and is at the time of puncturing located in a defined position relative to the lancet drive (and thus to the puncturing path) and rests against the surface of the skin with a contact surface thereof such that a puncture wound with a defined puncturing depth is generated by the puncturing motion, and a reference element coupling mechanism that is coupled to the lancet drive for moving the reference element.

In order to obtain a sufficient amount of blood for diagnostic purposes by a puncture that is associated with as little pain as possible, the optimal puncturing depth is of central importance. Variations of 0.05 mm can lead to significant changes in the pain sensation and/or amount of blood obtained in a puncture.

In the case of lancet devices with rotor lancet drive, the motion of the lancet is controlled precisely through the coupling to the drive rotor, as described. In this context, the puncturing depth corresponds to the distance between the lowest point (point of reversal) of the lancet motion and the plane of a skin contact surface. Known devices have a ring-shaped contact surface which surrounds an opening at the front end of the housing. The contact surface is pressed against the body part from which blood is to be withdrawn. Its axial position (i.e. the position in puncturing direction) is adjustable to allow adjustment of the puncturing depth.

If the opening surrounded by the contact surface is only slightly larger than the diameter of the lancet, the puncturing depth is well reproducible, but the amount of blood obtained by a puncture is relatively small and insufficient, in particular for integrated systems, in which a blood sample is to be analyzed inside the lancet device. If the housing opening surrounded by the contact surface is larger, such that the skin bulges into it, a larger amount of blood can be obtained by a puncture due to a better circulation.

The inventors have found that, when using a stationary skin contact surface at the front end of the housing, it is often not possible to achieve optimal reproducibility of the puncturing depth, in particular when the skin bulges into the housing opening that is surrounded by the contact surface when a lancet device is pressed against the skin. In such a case the inner rim of the housing opening provides only an inaccurate reference for the puncturing depth. In the case of smaller housing openings, this effect is less pronounced, but only a smaller amount of blood is obtained and there is a higher chance of the lancet device becoming contaminated by blood exiting from the puncture wound.

Hitherto, it has been attempted to solve this problem by finding an optimal compromise for the internal diameter of the contact surface, i.e. the size of the housing opening. Deviating from this customary approach, a lancet device according to the invention comprises a reference element which is mobile (relative to the lancet and the housing) and rests against the skin of a patient by means of a contact surface during the puncture. A reference element coupling mechanism, provided in addition to the lancet coupling mechanism, serves for moving the reference element. At the time of puncturing, at least at the point of time at which the lancet tip reaches its maximum penetration into the skin, the mobile reference element is located in a defined position relative to the lancet drive. Based on the following description, it will be evident that a design of this type allows very good reproducibility of the depth of the puncture wound to be achieved despite the bulging of the skin.

The reference element of a lancet device according to the invention can be designed as a sample take-up unit comprising, adjacent to each other, a guiding means, in particular a guiding channel for the lancet and a sample reception channel for receiving a blood sample. From the sample take-up unit, the blood sample can be transferred to a further processing station (for example, for analysis). However, it is preferred that the sample take-up unit has a reaction zone with reagents as an integral component such that the sample take-up unit forms a complete analytical element. The reaction of the sample with the reagents in the reaction zone leads to a change of a physical state (for example to a color change or, in the case of electrochemical analytical elements, to a change of a flow of current) that can be used as the basis for determining the concentration of an analyte contained in the sample. Since analytical elements of this type are known, there is no need to describe the test principles in more detail herein. After a single use the analytical elements (or other sample take-up units) are disposed of. For this reason, possible contamination by blood exiting from the puncture wound is insignificant.

Since the orifice of the sample reception channel, through which the sample is taken up, is spatially separated from the orifice of the guiding channel, the sample take-up unit must be moved after the puncture such that the orifice of the sample reception channel is moved to the puncture wound for receiving the sample. This function is provided by the reference element coupling mechanism that is present in addition to the lancet drive coupling mechanism. In principle, it is possible to use the orifice of the lancet guiding channel also for the sample reception channel, such that the channels are not spatially separated and the motion illustrated above is not required. However, as part of the invention it was noted that it is more favorable to provide separate channels and move, for example by means of a pivoting motion, the orifice of the sample reception channel to the puncture wound after the puncture.

An alternative exemplary embodiment relates to cases in which the reference element is a multiply usable component of the lancet device. In this case, contamination of the reference element by blood exiting from the puncture wound is obviously undesirable. For this reason, according to a preferred development of the invention, the reference element is rapidly moved away from the puncture wound after the puncture before it becomes contaminated by exiting blood.

In the context of the invention, it was noted that the pressure by which the reference element is pressed against the skin during a puncture counteracts the exiting of blood from the puncture wound. This finding is utilized in that the reference element is moved away from the puncture wound by means of a sufficiently rapid movement before blood can exit and contaminate the reference element (to a bothersome degree).

Preferably, the reference element is moved at least 2 mm from the puncture wound within 50 milliseconds after the puncture. Such a fast returning motion of the reference element is preferably achieved by the drive rotor of the lancet drive. The lancet also must be moved at high speed to minimize the pain. For this reason, the reference element coupling mechanism preferably transforms a rotational motion of the drive rotor into a motion of the reference element, which preferably is a translational motion.

An important component of the lancet device according to the invention, which, however, is also important as a separate item, is a lancet drive assembly comprising a lancet drive with a drive rotor that can be driven by a drive spring and a tensioning rotor for tensioning the drive spring, a first lancet coupling mechanism for transforming a rotational motion of the drive rotor into a puncturing and returning motion of the lancet, and a further coupling mechanism that is coupled to the lancet drive.

The further coupling mechanism preferably serves for moving a reference element, but can also be used, for example, for performing an incremental step in the motion of a cartridge with test strips (for example in an analytical instrument with integrated lancet device), for application of an antiseptic to the puncturing site or for reception of a sample on a test field.

BRIEF DESCRIPTION OF THE DRAWINGS

The invention is illustrated in more detail hereafter on the basis of exemplary embodiments that are shown in the figures. The features described therein can be used individually or in combination in order to generate preferred embodiments. Identical or corresponding components are identified by consistent reference numbers. In the figures:

FIG. 2a shows a schematic detailed cross-sectional view of the lancet device shown in FIG. 2;

DETAILED DESCRIPTION

Figure 1:
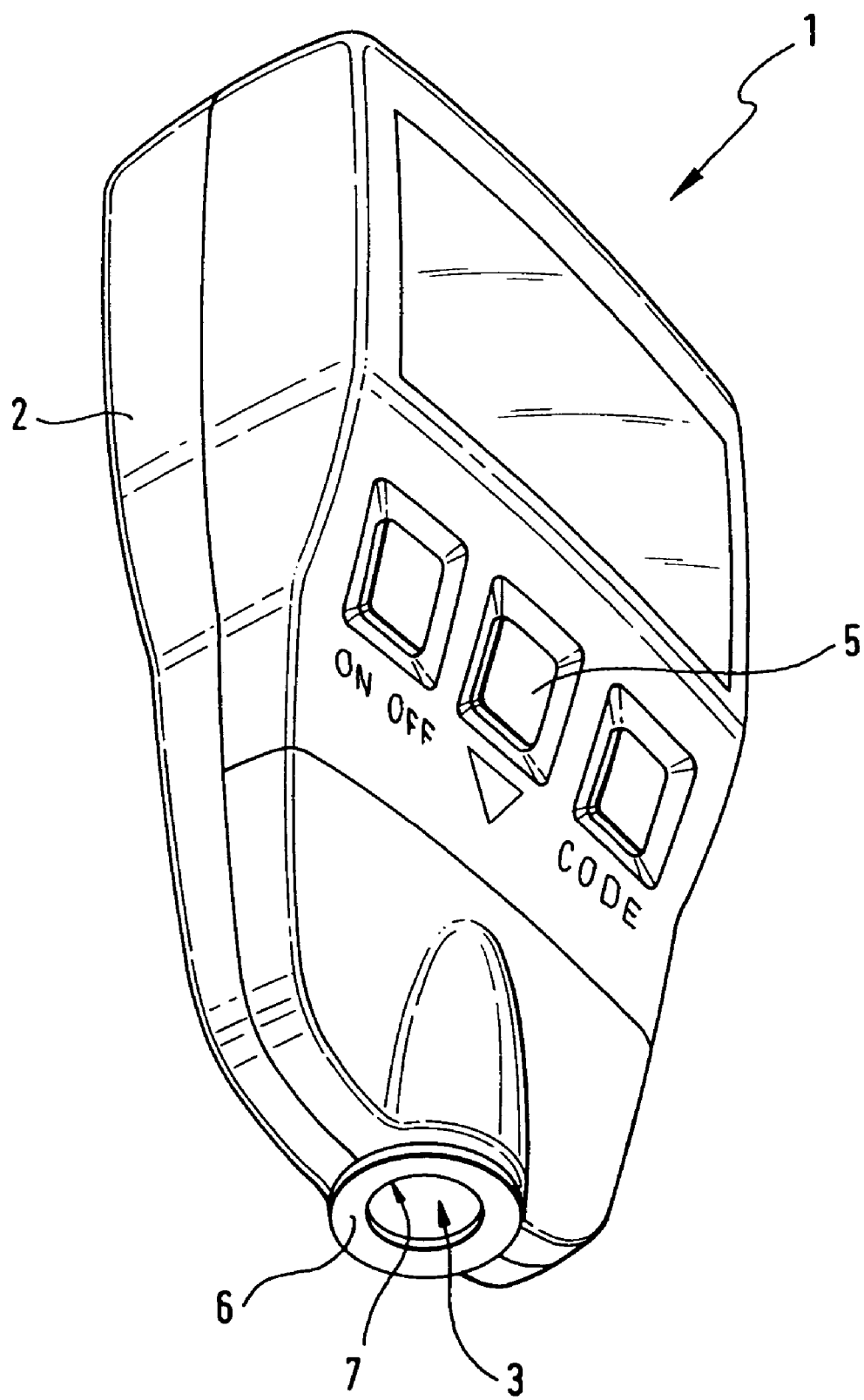
FIG. 1 shows a perspective view of a lancet device.

The lancet device 1 shown in FIG. 1 serves to generate a puncture wound for withdrawing blood for diagnostic purposes. Its housing 2 comprises a housing opening 3. A puncture wound may be generated in a body part that is placed in front of the housing opening by the tip of a lancet that can be moved on a puncturing path in the housing 2.

The housing opening 3 is surrounded by a ring-shaped contact surface 6 that is used to press the lancet device against a body part, for example a finger tip, for a puncture. Thereby the surface of the skin bulges into the housing opening 3. The bulging of the skin promotes the exiting of blood such that even at a relatively small puncturing depth of 0.5 mm to 2 mm a sufficient amount of blood for diagnostic purposes can be withdrawn. By repeatedly pressing the device against the skin, this effect can be improved further ("pumping effect"). Moreover, a blood withdrawal device with this design can be used to withdraw a drop of blood even from body parts that are not so well-supplied with blood, but are less sensitive to pain. In order to provide for the desired pumping effect, the internal diameter of the contact surface 6 should be relatively large, preferably at least 7 mm or even at least 9 mm.

Preferably, the contact surface 6 tapers inwards towards the housing opening 3. In particular, it is advantageous to make the contact surface 6 from a deformable material, for example polyurethane or rubber, which allows an even better pumping effect upon pressing against a body part as mentioned above. More details and alternative embodiments of the contact surface 6 are described in DE 100 26 172 A1, which in this respect is incorporated herein by reference. Therein, the contact surface is provided by a component termed compression unit owing to its pumping effect.

As a result of the described design the exact position of the surface of the skin relative to the lancet device is a function of the pressure by which the device is pressed against the skin and further factors (for example, skin tension). It is therefore not exactly defined. Based on FIGS. 2 and 3, it shall be illustrated hereafter how it can be ensured that a puncture wound with a predetermined puncturing depth is generated during the puncturing motion of the lancet.

Figure 2:
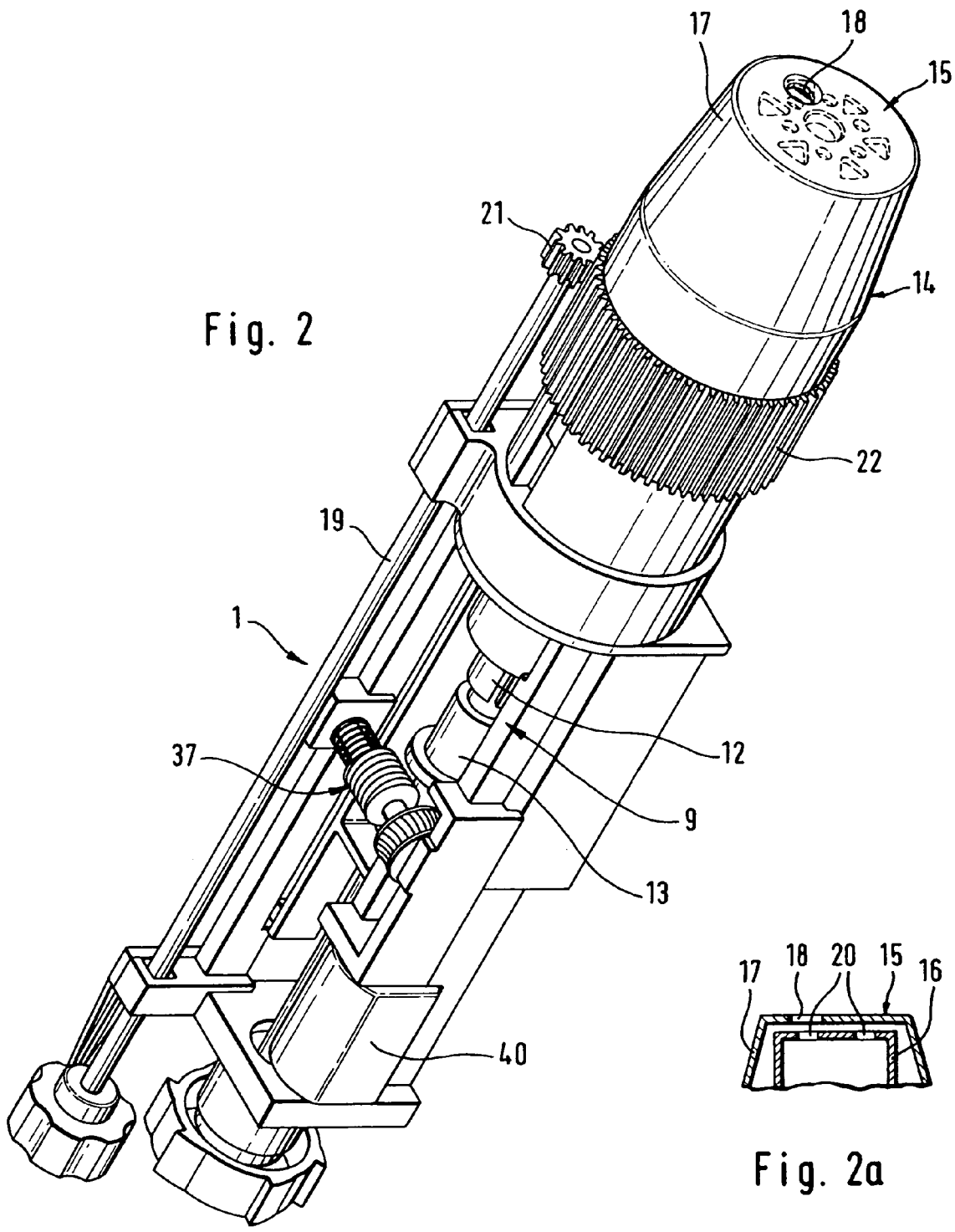
FIG. 2 shows a perspective view of a lancet device with the housing removed.
Figure 3:
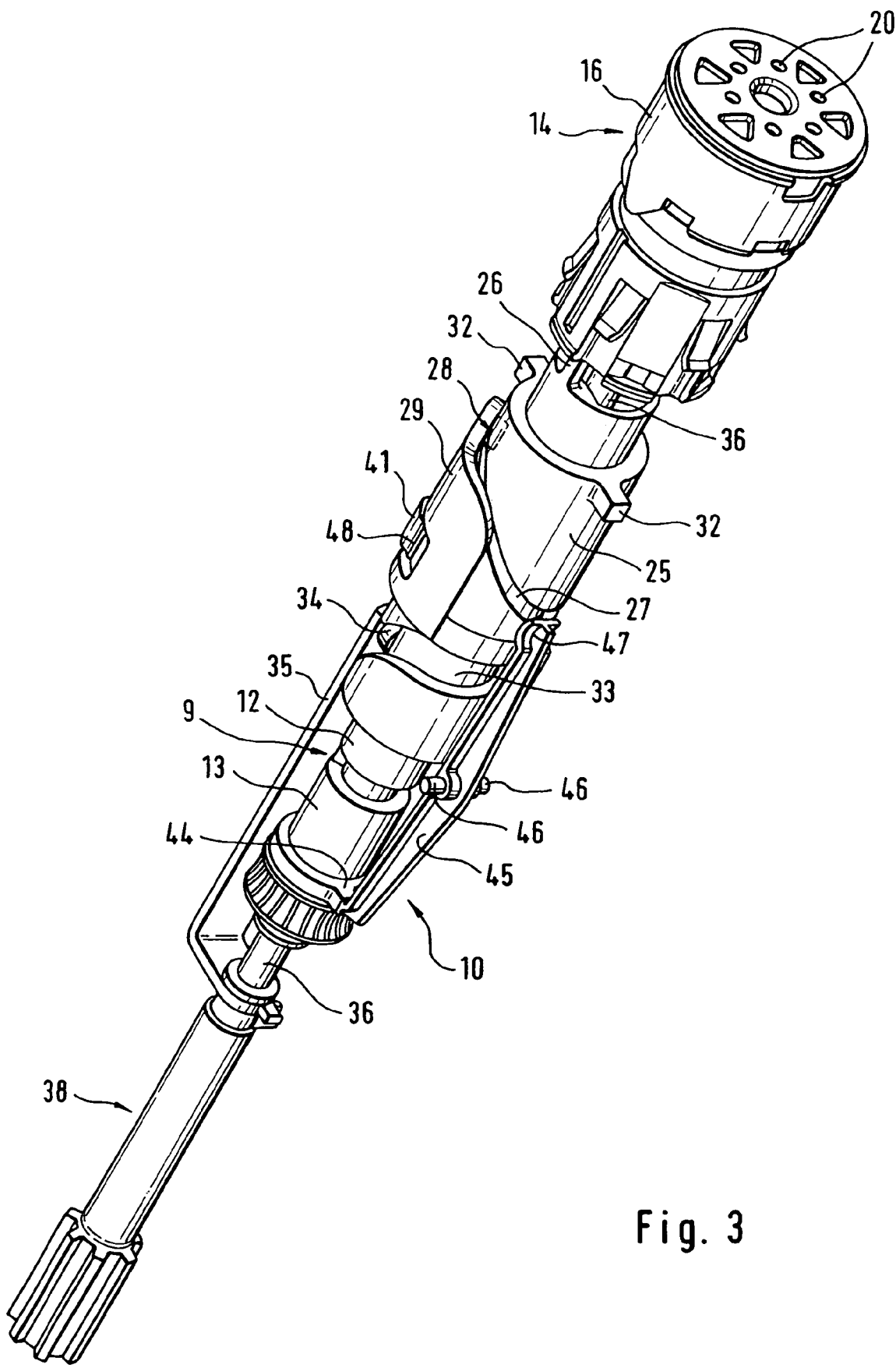
FIG. 3 shows a perspective view of a lancet drive assembly with a drum cartridge.

FIG. 2 shows a lancet device 1 with the housing removed; FIG. 3 shows its lancet drive assembly 10 that is combined with a drum cartridge 16. The assembly 10 comprises a drive rotor 12 that can be driven by a drive spring, and a tensioning rotor 13 for tensioning the drive spring. For clarity of the illustration, the drive spring that is arranged between the drive rotor 12 and the tensioning rotor 13 is not shown in FIGS. 2 and 3. The drive spring 11 is shown only in FIG. 4. It is a torsion spring that is pre-tensioned and hinged with one of its ends to the drive rotor 12 and with the other end to the tensioning rotor 13.

A further component of the lancet drive assembly 10 is a output-side lancet coupling mechanism 24 that transforms, in a drive phase of the lancet drive, the rotational motion of the drive rotor 12, which can be rotated about an axis, into a puncturing motion in which the lancet is moved in the puncturing direction at high speed in order to generate a puncture wound. Likewise, the returning motion of the lancet is driven and controlled by the rotational motion of the drive rotor 12 by means of the lancet coupling mechanism 24. During the entire drive phase (which comprises the puncturing and returning motion), the end of the drive spring facing away from the drive rotor 12 is supported against the tensioning rotor, which is arrested in the drive phase such that it cannot be rotated backwards (against the direction of rotation of the drive rotor). For tensioning of the drive spring, in a tensioning phase of the lancet drive motion, the tensioning rotor can be rotated, while the rotation of the drive rotor 12 is impeded, in the same direction of rotation, in which the drive rotor rotates during the drive phase. A lancet drive of this type is described in EP 1384438 A1, the content of which, in particular as regards the details of the lancet drive, are herewith incorporated into the present application by way of reference.

Moreover, the lancet drive assembly 10 comprises a further coupling mechanism 38 that allows a rotational motion of a rotating component of the lancet drive to be transformed into a motion of the reference element 14 or any other component of a lancet drive. Since this further coupling mechanism 38 serves, in the exemplary embodiment described, for moving the reference element 14, it is termed "reference element coupling mechanism" in this context.

The reference element is mobile or moveable relative to the lancet and relative to the housing. It is provided and arranged such that its contact surface rests against the surface of the skin of a patient in a defined position relative to the lancet drive at the time of puncturing of the skin. This ensures that a puncture wound is generated that has a predetermined puncturing depth that corresponds to the distance between the contact surface of the reference element and the most extended (lowest) position of the lancet tip in the direction of puncturing.

Figure 4:
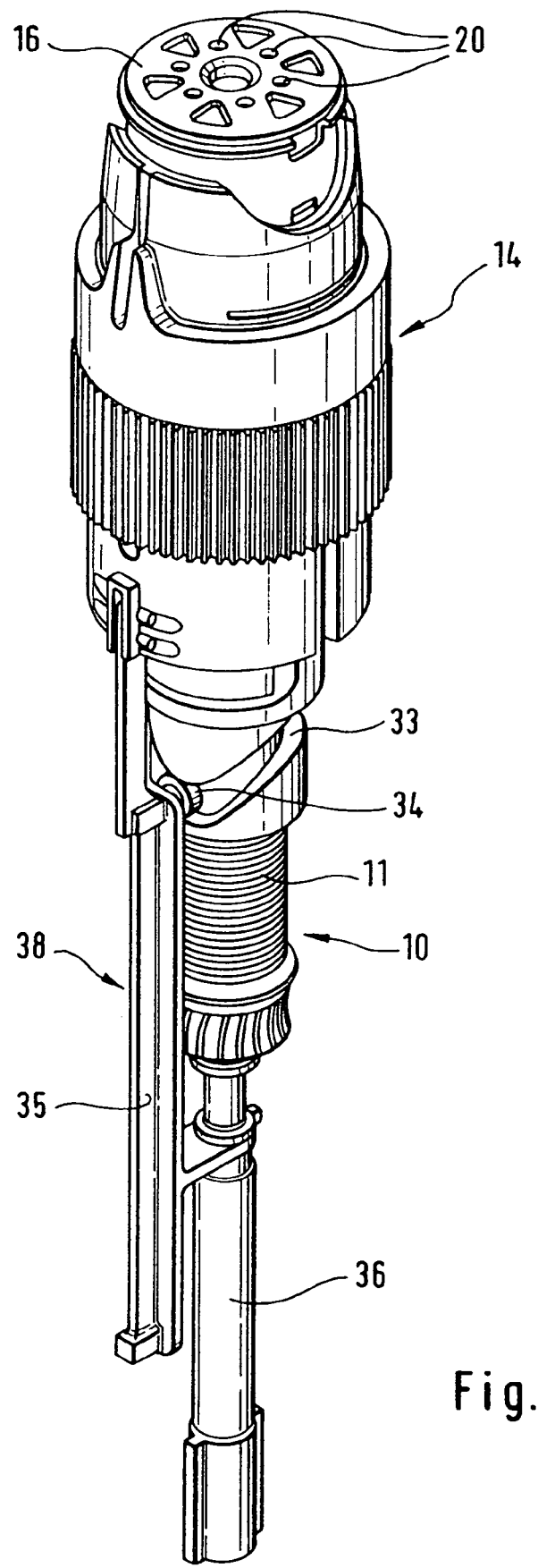
FIG. 4 shows a further perspective view of the exemplary embodiment shown in FIGS. 2 and 3.

In the exemplary embodiment shown in FIG. 2, the reference element 14 comprises a drum cartridge 16, in which a plurality of lancets can be stored, and a protective cap 17 surrounding the drum cartridge 16. The contact surface 15 is provided on the protective cap 17 by which the reference element 14 rests against the surface of the skin. As shown, particularly in the schematic view of the front part of the reference element 14 in FIG. 2, a lancet opening 18 is provided in the contact surface 15 through which the lancet exits in a puncture in order to generate a puncture wound in a finger that is pressed against the housing opening 3 (i.e. against contact surface 6). FIG. 4 shows the reference element 14 with its protective cap 17 removed and shows the connection of the reference element to the reference element coupling mechanism 38.

For sterile storage of lancets until use, it is preferred for the drum cartridge 16 to comprise a plurality of chambers, in each of which a single lancet is stored. However, it is also possible to arrange the lancets inside a drum cartridge 16 in a ring that is not subdivided into individual chambers. The number of lancets stored in a drum cartridge 16 is virtually freely selectable. Preferably, the drum cartridge 16 contains three to twelve, particularly preferably four to eight, lancets. The drum cartridge 16 can be rotated relative to the lancet opening 18 of the protective cap 17 such that exit openings 20 of the drum cartridge 16 can be positioned in registration with the lancet opening 18 in a consecutive order for a puncture.

The lancet coupling mechanism 24 also includes a pushing cylinder 25 that is attached to the housing such that it can not rotate. A connecting arm or coupling rod 26 extends from the cylinder 25 and is, during the puncturing and return motion, connected to an active lancet. The lancet coupling mechanism 24 transforms the rotational motion of the drive rotor 12 by means of curve steering into a translational motion of the active lancet.

For this purpose, the pushing cylinder 25 is provided with a recess in the form of a groove that forms the steering curve 27 and along which travels a steering curve traveler 28 of the drive rotor 12. In the embodiment shown, the steering curve traveler 28 is provided in the form of a steering peg which engages the groove and sits on the end of a steering arm 29 that originates on the drive rotor 12. The pushing cylinder 25 is provided with guiding elements 32 that engage axially-extending longitudinal grooves in the inner wall of the housing 2 (not shown) in order to provide for the pushing cylinder 25 to be connected to the housing 2 such that it is locked against rotation but mobile in the puncturing direction. In the embodiment shown, the guiding elements 32 are implemented in the form of two guiding pegs.

The reference element coupling mechanism 38, described hereafter with reference to FIGS. 3 and 4, is used to retract the reference element 14 from the puncture wound after a puncture, and also operates by means of a curve steering. Its steering curve 33 is formed by a recess in the drive rotor 12 in the form of a groove that is engaged by a steering curve traveler 34 in the form of a steering peg. By means of a coupling arm 35, it is connected to a guiding rod 36 to which the drum cartridge 16 is attached. The coupling arm 35 carries the reference element 14. The guiding rod 36 can be rotated relative to the coupling arm 35 such that the drum cartridge 16 can be rotated in the reference element 14 by means of the guiding rod 36. Thus, the lancets stored in the drum cartridge 16 can be used consecutively.

For setting the puncturing depth, the distance between the drum cartridge 16 and the protective cap 17 forming the contact surface 15 is changed by adjusting the length of the reference element 14 by means of a thread (not shown). This setting is carried out by means of the shaft 19 shown in FIG. 2, which engages, via a toothed wheel 21, a toothed rim 22 of the reference element 14.

For tensioning of the drive spring, the tensioning rotor 13 is rotated by means of a gearing 37 that is preferably driven by a battery-driven electrical motor 40 (FIG. 2). However, the tensioning rotor 13 can also be driven manually by means of a shaft that projects from the housing 2.

In order to be able to utilize the spring force of the drive spring 11 as efficiently as possible for a rapid puncturing and returning motion, it has proven to be advantageous to carry out preparatory motions of the lancet and of the reference element 14 before the tensioning or no later than during the tensioning of the drive spring.

For this reason, the drive rotor 12 and the tensioning rotor 13 initially rotate through a preparatory range of rotation angles in a preparatory phase before the drive spring is tensioned. In the process, a rotational motion of the tensioning rotor 13 is transferred by means of the pre-tensioned drive spring to the drive rotor 12 such that the latter is rotated jointly (i.e. concurrently, though not necessarily, but preferably, synchronously) with the tensioning rotor 13 in at least a part of the preparatory phase. By means of one of the coupling mechanisms the motion of the drive rotor 12 in the preparatory range of rotation angles is transformed into a preparatory motion of the coupling rod 26 relative to the drum cartridge 16, in which the coupling rod 26 penetrates through an insertion opening (not shown) located opposite from the lancet opening 18 to enter one chamber of the drum cartridge 16 and locks with one lancet that is situated therein. Further details and alternative embodiments of a suitable coupling mechanism are described in WO 02/36010 A1, which is hereby incorporated into the present application, in this respect, by way of reference.

While the drive rotor 12 and the tensioning rotor 13 run through the preparatory range of rotation angles, the reference element coupling mechanism 38 advances the reference element 14 in the housing 2 in the direction of its housing opening 3 to such an extent that its contact surface 15 can rest against the skin of a patient. Owing to the size of the internal diameter of the contact surface 6, the tip of the finger placed against the contact surface 6 bulges slightly into the housing opening 3 of the lancet device 1 (FIG. 1). Consequently, the contact surface 15 of the reference element 14 can rest against the skin even though it is situated inside the housing in a position in which the contact surface 15 is located at a distance behind a plane extending through the inner rim 7 of the contact surface 6.

Once the drive rotor 12 has rotated through the preparatory range of rotation angles, it is locked by means of a locking element 41 such that the drive spring is tensioned upon further rotation of the tensioning rotor 13, during the subsequent tensioning phase of the lancet drive motion. In the embodiment shown, the locking element 41 is provided as a trigger tongue that rests resiliently against an internal wall of the housing 2 and originates from the drive rotor 12 and engages a recess in the internal wall of the housing for locking the drive rotor 12. The trigger tongue and the steering arm 42 with the steering peg 28 are manufactured as a single-part in the form of an injection molded part.

When the drive rotor 12 is locked by the locking element 41, any further rotation of the tensioning rotor 13 causes tensioning of the drive spring. Electrical contacts (not shown) are situated on the tensioning rotor 13 for shutting off the electrical motor 40 once the tensioning rotor 13 has run through a predetermined tensioning angle range. This completes the tensioning phase. If the tensioning rotor 13 is driven manually, it can be locked by mechanical locking means after it was rotated through the tensioning angle range.

After completion of the tensioning process, a puncturing motion is initiated by releasing the locking element 41 from its locking engagement such that the drive rotor 12, driven by the drive spring in the drive phase, very quickly rotates to its resting position. It rotates in the same direction as the tensioning rotor 13 when it tensions the drive spring. This rapid motion of the drive rotor 12 is transformed by means of the lancet coupling mechanism 24 into a puncturing and returning motion of the lancet and by means of the reference element coupling mechanism 38 into a returning motion of the reference element 14.

The returning motion of the reference element 14 and the returning motion of the lancet each are a translational motion in axial direction. By utilizing the rapid motion of the drive rotor 12 for the returning motion of the reference element 14 as well as the returning motion of the lancet, the reference element 14 is removed from the puncture wound sufficiently fast to essentially avoid contamination by exiting blood.

The puncturing process can be initiated (triggered), for example, by pressing the contact surface 15 of the reference element 14 against the skin with a predetermined minimal force. Preferably, the reference element 14 comprises a pressure sensor that can be used to generate a signal required for triggering the puncturing motion once a pressure in excess of a predetermined minimal pressure is applied to the contact surface 15. The pressure sensor can be implemented, for example, by bearing the contact surface 15 on a spring such that electrical contact is made only upon compression of the spring.

Alternatively or in addition, a trigger button 5 can be arranged on the housing 2 of the lancet device 1 (FIG. 1). In order to start a puncturing process in the embodiment shown, an electrical signal is initially generated by means of which the electrical motor 40 is activated. This causes the tensioning rotor 13 to be rotated by an increment of rotation angles. As is evident from FIG. 3, the tensioning rotor 13 comprises a trigger cam 44 that actuates a trigger mechanism 45 once the tensioning rotor 13 is rotated beyond a predetermined rotation angle position, whereby the previously existing locking of the drive rotor 12 is released.

In the embodiment shown, the trigger mechanism 45 is provided in the form of a rocker that is attached to the housing 2 such as to be capable of pivoting about bearing peg 46. The trigger cam 44 of the tensioning rotor 13 lifts one end of the rocker 45 and lowers the other end of the rocker 45 on which a head part 47 is situated. The locking element 41 comprises a shoulder with a returning surface 48. In this phase of motion (not shown in FIG. 3), the head part 47 is situated above the locking element 41 and presses onto the returning surface 48 of the trigger tongue 41, whereby the latter is released from its engagement in the recess of the housing 3. As soon as the locking element 41 no longer blocks the drive rotor 12, the drive spring relaxes such that the drive phase of the motion of the lancet drive proceeds.

Figure 5:
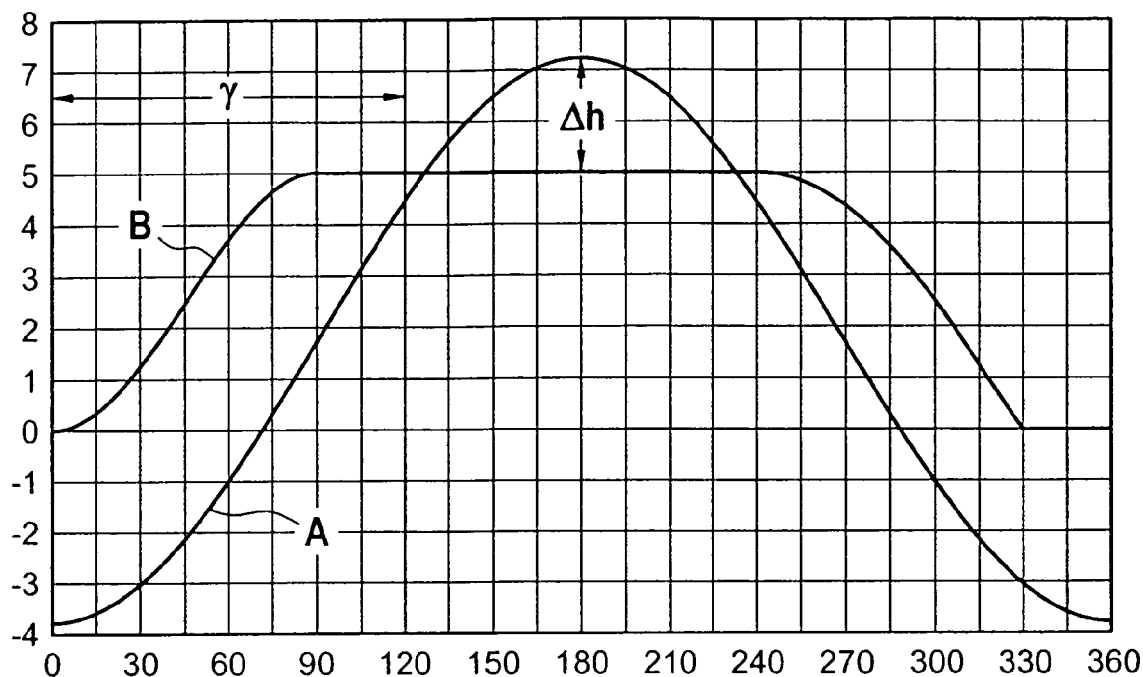
FIG. 5 shows a graphical view of the motion of the lancet and of the reference element in the assembly of FIG. 3 as a function of the rotational angle position of the drive rotor.

FIG. 5 illustrates the motions of the lancet and of the reference element 14 which are driven and controlled by the rotational motion of the drive rotor 12 by means of the coupling mechanisms 24, 38. In FIG. 5, the travel, i.e. the motion in axial direction, of the coupling rod 26 is plotted as curve A and the travel of the reference element 14 is plotted as curve B versus the rotation angle position of the drive rotor 12. The figure shows a full working cycle of the lancet drive which comprises a rotational motion of the drive rotor by a total of 360°. A working cycle commences with the start of a rotational motion of the tensioning rotor and concludes at the end of the returning motion of the lancet after the puncture.

In the beginning of the working cycle, the drive rotor 12 runs through a preparatory range of rotational angles γ (in a relatively slow motion simultaneous with the tensioning rotor, as described supra). It ends at about 120° (indicated by a vertical line in FIG. 5). The motion of the drive rotor 12 in the preparatory range of rotation angles is transformed by means of the two coupling mechanisms 24, 38 such that both the coupling rod 26 and the reference element 14 are moved forward (in the direction to the housing opening 3) in the device until the contact surface 15 of the reference element 14 rests against the skin and the coupling rod 26 is coupled to a lancet.

Since the contact surface 15 rests against the skin at the time of the puncture, the depth of the puncture wound is predetermined precisely by the section Δh of the coupling rod travel that extends beyond the contact surface 15. After the puncture, the coupling rod 26 and the reference element 14 are retracted to their starting positions. Movement through the drive range of rotational angles, which follows the preparatory range of rotation angles (and corresponds to the drive phase of the lancet drive motion, consisting of the puncturing and returning motion) takes place in less than 100 ms, preferably less than 20 ms.

Figure 6:
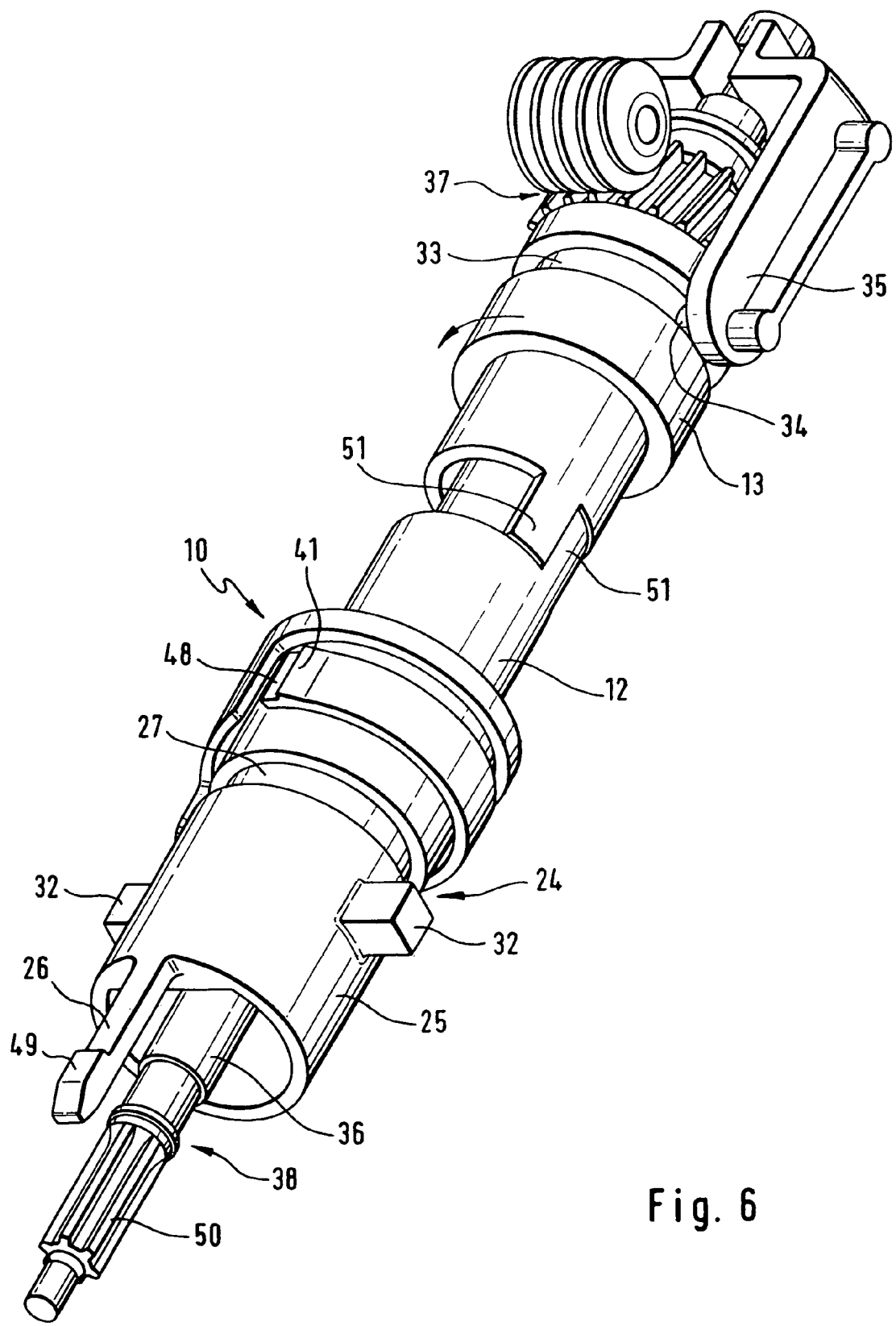
FIG. 6 shows a perspective view of a further exemplary embodiment of a lancet drive assembly.

FIG. 6 shows a further embodiment of a lancet drive assembly 10. The reference element 14 is not shown in FIG. 6, for better visibility of the head 50 of the guiding rod 36, onto which the drum cartridge 16 is plugged, and of the coupling rod 26 that locks with a lancet for a puncture. It is also evident that the coupling rod head 49 comprises an enlargement that allows form-fitting coupling to a lancet. Like the exemplary embodiment described with regard to FIGS. 2 and 3, the drive spring, arranged between the drive rotor 12 and the tensioning rotor 13, is not shown.

FIG. 6 shows that the drive rotor 12 and the tensioning rotor 13 comprise stop parts 51 that abut against each other in a stop position of the rotors 12, 13 and thus stop a rotational motion of the drive rotor 12 relative to the tensioning rotor 13. Stop parts 51 of this type are also present in the embodiment described previously. They serve, in particular, for bearing the pre-tension of the drive spring and stopping the drive rotor 12 at the end of the puncturing and returning motion.

As mentioned earlier, in the preparatory rotation angle range, a rotational motion of the tensioning rotor 13 is transferred by the drive spring 11 to the drive rotor 12 such that the tensioning rotor 13 and the drive rotor 12 rotate jointly in this range of rotation. Pre-tensioning the drive spring 11 allows a tight coupling of the tensioning rotor 13 to the drive rotor 12 such that the rotation angle position of the tensioning rotor 13 deviates from the rotation angle position of the drive rotor 12 by no more than 10°, preferably no more than 5°, during the joint rotation. Sufficiently high pre-tension of the drive spring 11 is thus used to achieve a largely synchronous motion, i.e. with the same angle and velocity, of the two rotors. This is advantageous in that the motions of the coupling mechanisms 24, 38 can be controlled even more precisely. Alternatively, synchronous motion of the two rotors 12, 13 can be achieved also by rigid coupling means (not shown) operating while they run through the preparatory range of rotation angles.

Other details of this embodiment are also largely the same as in the embodiment described with reference to FIGS. 2 to 4. In this context, one difference is that the reference element coupling mechanism 38 transforms a rotational motion of the tensioning rotor 13 (not of the drive rotor) into a motion of the reference element 14. For this reason, the steering curve 33 of the reference element coupling mechanism 38 (again embodied as a groove-shaped recess) is provided in the tensioning rotor 13. In this design, the reference element coupling mechanism 38 is not utilized for a rapid returning motion of the reference element 14 after the puncture, but rather for precise setting of the puncturing depth by a slow motion of the reference element 14. As is illustrated in FIG. 5, the puncturing depth is a function of the position of the contact surface 15 of the reference element 14 relative to the coupling rod 26 at the time of puncture. In order to set the puncturing depth, the reference element 14 is moved in axial direction relative to the coupling rod 26 prior to a puncture. This setting motion proceeds independent of the puncturing motion and can be performed as a slow motion. Preferably the set position shall not change during the complete puncturing motion. For this reason, the reference element coupling mechanism 38 preferably is preferably coupled to the tensioning rotor 13 that moves relatively slowly.

Figure 7:
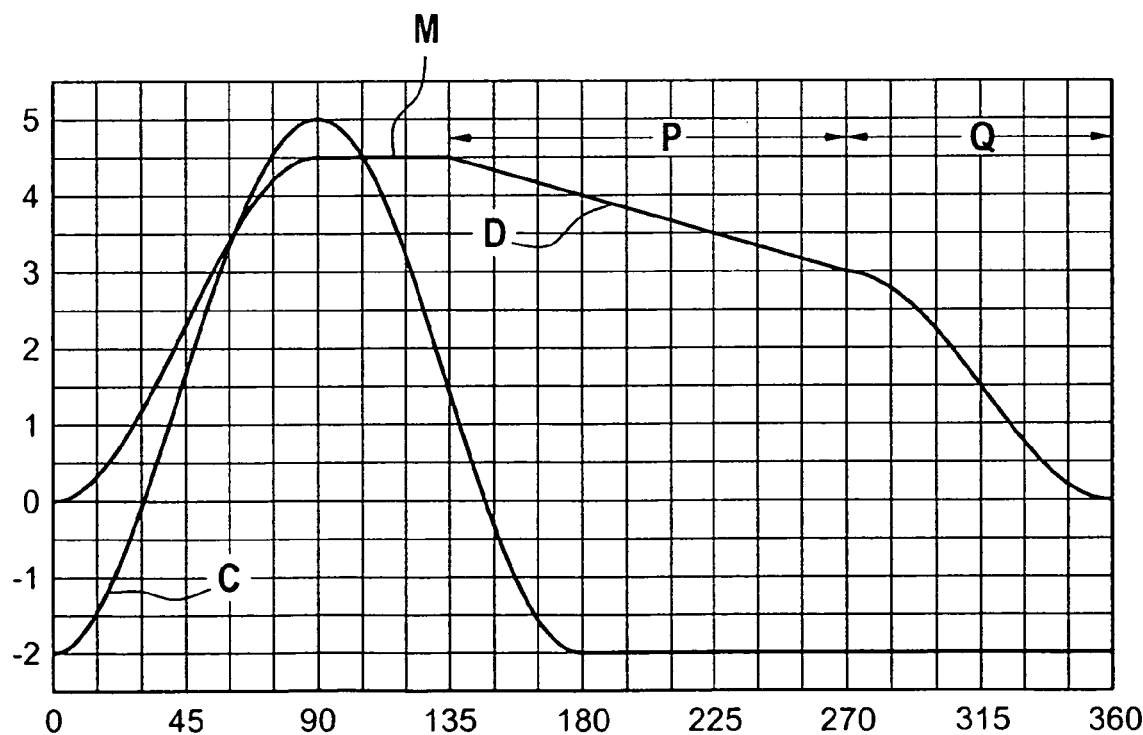
FIG. 7 shows a graphical view of the motion of the lancet and of the reference element in the assembly of FIG. 6 as a function of the rotational angle position of the tensioning rotor.

FIG. 7 shows the motion of the coupling rod 26 and thus the motion of the lancet in the form of curve C and the motion of the reference element 14 as curve D as a function of the rotation angle position of the tensioning rotor 13.

It is preferable for the puncturing depth to be set after the tensioning. A first section of the steering curve 33 of the reference element coupling mechanism serves to initially move the reference element 14 into a maximum position M which corresponds to a minimal penetration depth during puncture. If the tensioning rotor 13 is subsequently rotated further, the reference element 14 is retracted from this maximal position to a position that corresponds to the desired puncturing depth ("puncturing position"). The more the reference element 14 is retracted relative to the coupling rod 26, the larger is the depth of the subsequent puncture. Once the puncturing position with the desired puncturing depth is reached, the electrical motor 40 is shut off and the tensioning rotor 13 is locked in this position. After triggering, the tensioning rotor 13 concludes its working cycle by being rotated in the motion section Q until it reaches its original position.

In the procedure for setting the puncturing depth described above, it is very important that the rotation angle position of the tensioning rotor 13 is locked exactly in the desired position. Inaccurate positioning of the rotation angle position of the tensioning rotor 13 leads to a corresponding inaccuracy in the set puncturing depth. In the embodiment shown, the electrical motor 40 drives the tensioning rotor 13 by means of a two-step worm gear pair 37 such that the rotation angle position of the tensioning rotor 13 can be adjusted precisely by electronic counting of the revolutions of one or more parts of the worm gear pair 37.

The exemplary embodiments of FIGS. 2 to 4 and 6 can be combined such that a first reference element coupling mechanism couples the reference element 14 to the tensioning rotor 13 in order to set the puncturing depth prior to triggering a puncturing motion, and a second reference element coupling mechanism couples the reference element 14 to the drive rotor 12 in order to move the reference element 14 after a puncture. Thus, the drive spring is utilized for a rapid returning motion, which would be difficult to implement by means of an electrical motor 40, whereas the electrical motor 40 is utilized for a slow puncturing depth setting motion for which purpose the drive spring would be less well-suited.

It is also possible to couple the reference element 14 to the tensioning rotor 13 in order to move it into a desired position in preparation of a puncturing motion, and to provide a separate returning spring for the returning motion of the reference element 14, which returning spring is tensioned by the tensioning rotor 13 during the advancement of the reference element 14. The force of the tensioned returning spring can be borne, for example, by the reference element 14 being latched in the desired position on the housing. In this context, the retraction of the skin reference after a puncture, i.e. the unlatching, can be triggered by the drive rotor 12, preferably by the tensioning rotor 13.

Figure 8:
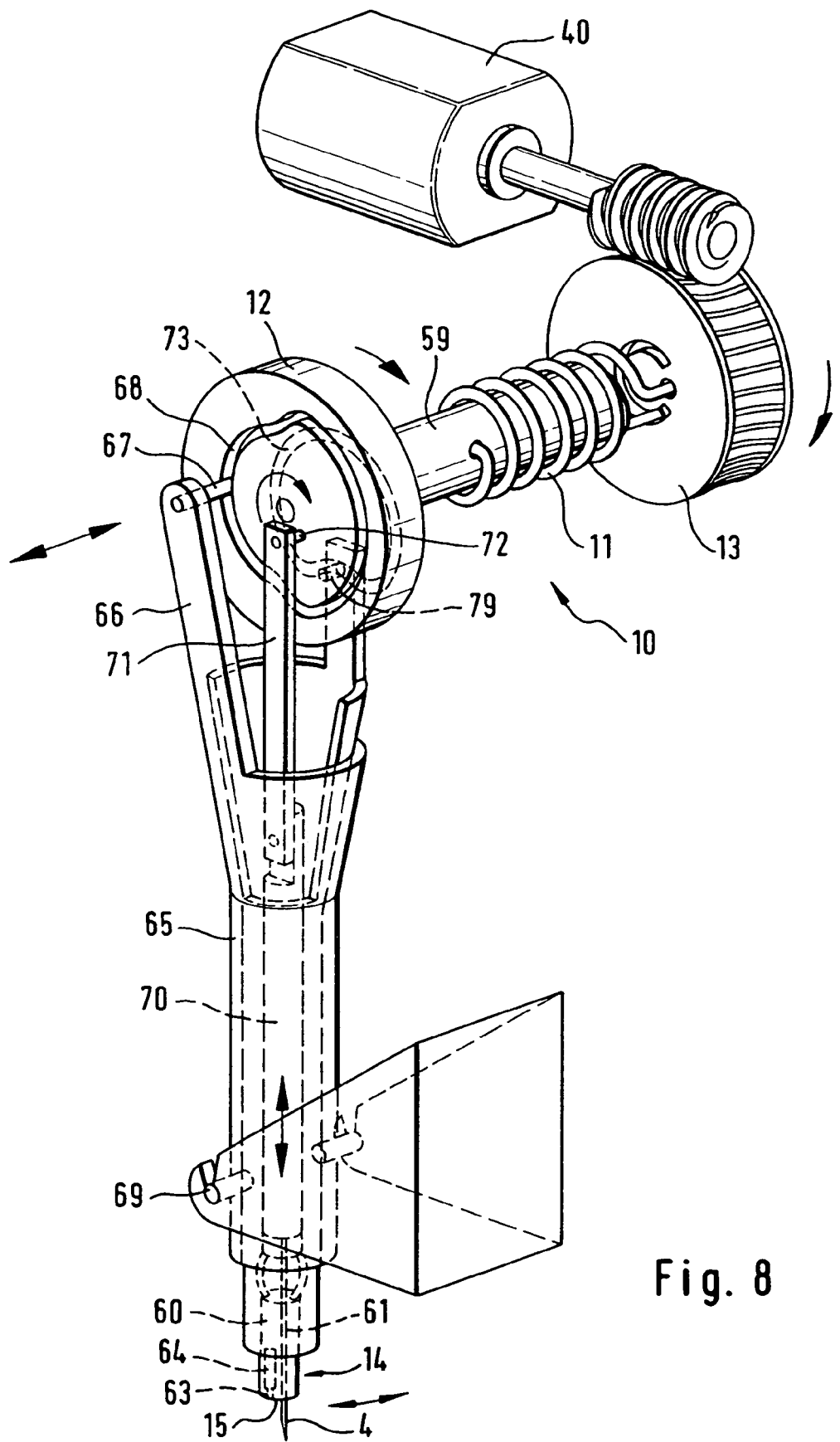
FIG. 8 shows a perspective view of a further exemplary embodiment of a lancet drive assembly.
Figure 9:
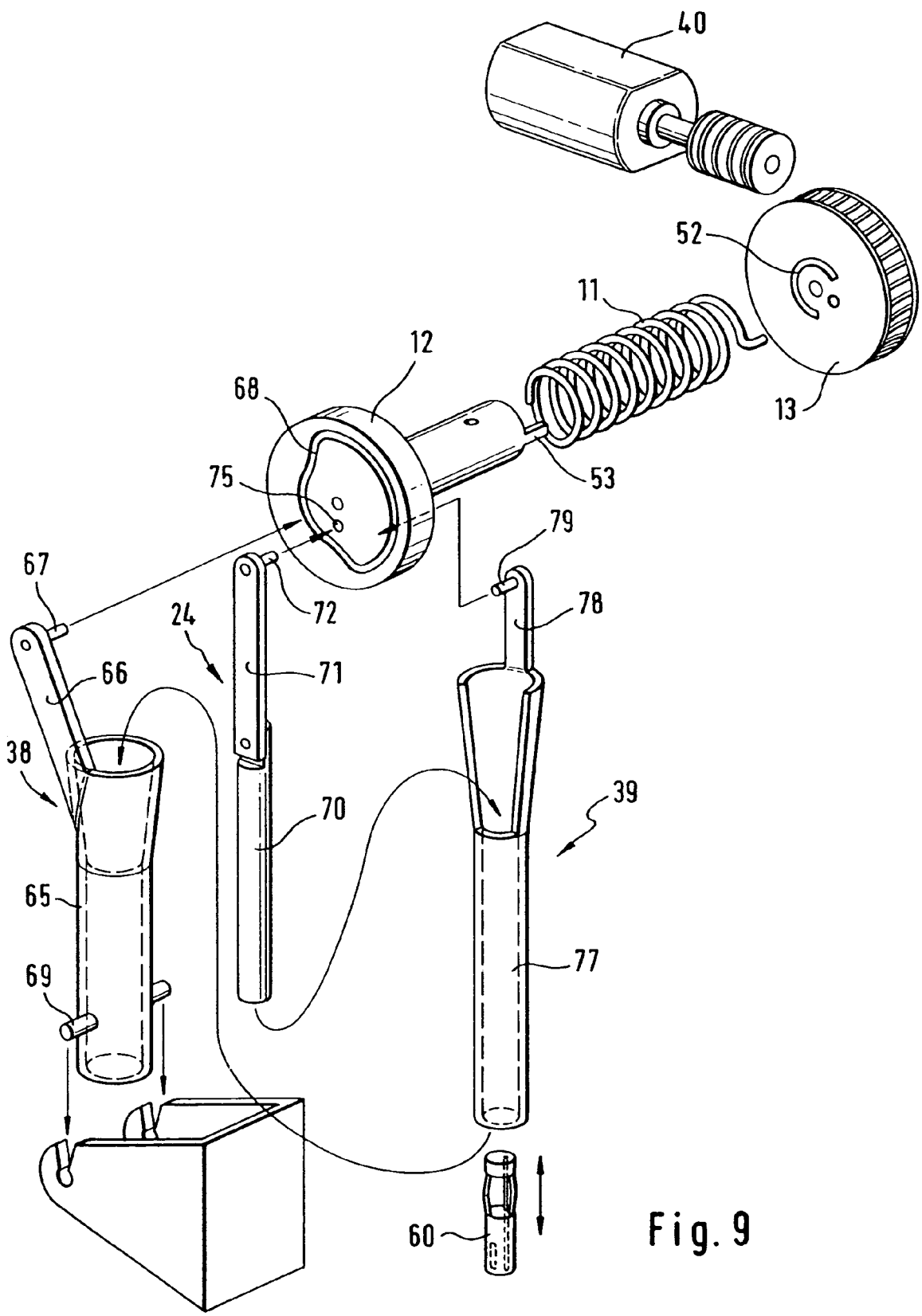
FIG. 9 shows a perspective exploded view of the parts of the exemplary embodiment shown in FIG. 8.
Figure 10:
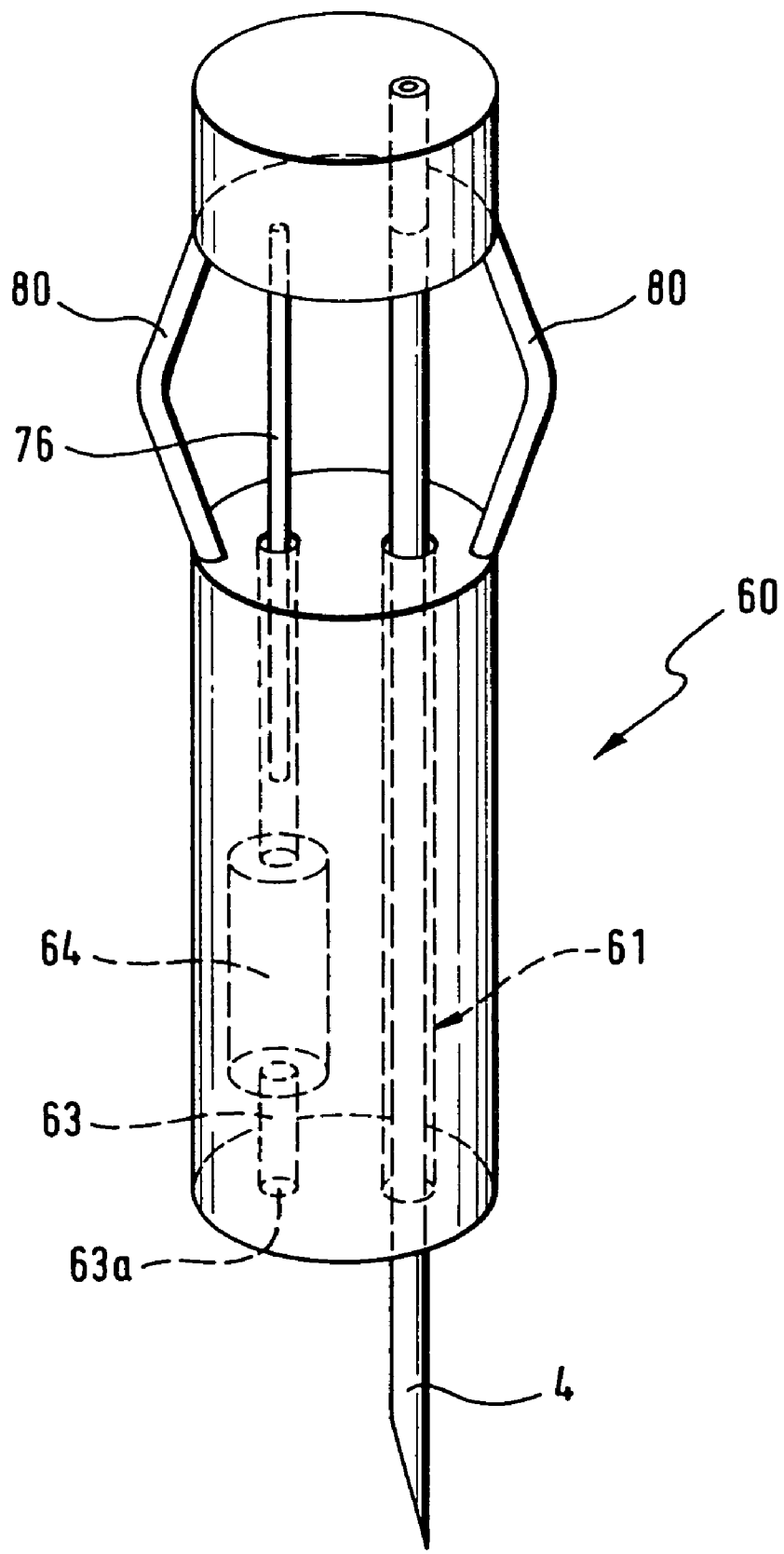
FIG. 10 shows a schematic view of a reference element in the form of a sample take-up unit.

FIGS. 8 and 9 show a further embodiment of a lancet drive assembly 10. Differing from the embodiments described thus far, the reference element 14 is provided in this embodiment in the form of a sample take-up unit 60. As is shown more clearly in FIG. 10, the sample take-up unit 60 comprises a guiding channel 61 for the lancet 4 and a sample reception channel 63 with an orifice 63a for receiving a sample. The sample take-up unit 60 further comprises a reaction zone 64 with reagents to which the sample is supplied through the sample reception channel 63.

Like in the other embodiments, the lancet drive assembly 10 comprises a drive rotor 12 that can be driven by a drive spring 11 and can rotate about an axis 59, and a tensioning rotor 13 for tensioning the drive spring 11. Drive rotor 12 and tensioning rotor 13 are arranged to be coaxial. In the exemplary embodiment shown in FIGS. 8 and 9, the drive spring 11 is a leg spring provided in the form of a helical spring. Alternatively, a spiral spring serving as drive spring 11 is also feasible.

The windings of the drive spring 11 can be wound with a distance to each other in order to minimize frictional losses, or close to each other in order to attenuate rotational vibrations. A pre-tension in the direction of pull provides for attenuating friction between the windings.

In order to bear the pre-tension of the drive spring 11, the tensioning rotor 13 comprises a stop part in the form of a stop groove 52 that is engaged by a stop peg 53 of the drive rotor 12. The pre-tension presses the stop peg 53 against an end of the circular arc-shaped stop groove 52 onto which it abuts in its resting position.

After a puncture, an orifice 63a (FIG. 10) of the sample reception channel 63 is moved to the generated puncture wound in order to allow take-up of the sample liquid exiting from the wound. For this purpose, the reference element coupling mechanism 38 comprises a bushing 65 that is suspended for pivoting about two bearing pegs 69. A rigid steering arm 66 of the bushing 65 has a steering peg which engages, acting as steering curve traveler 67, a steering curve 68 of the drive rotor 12 that is formed by a groove-like recess. The steering curve 68 has two semicircular sections with different radii. The steering curve traveler 67 moving between these two sections causes the bushing 65 to perform a pivoting motion. The coupling rod 70 of the lancet coupling mechanism 24 can carry out a translational motion in the bushing 65 in order to provide the puncturing and returning motion of the lancet 4. The coupling rod 70 is driven by the drive rotor 12 via a connecting rod 71. The connecting rod 71 carries a crank pin 72 that engages a bore hole 75 of the drive rotor 12.

In order to take up, by the sample reception channel 63 of the sample take-up unit 60, as much sample liquid exiting from the puncture wound as possible, the exemplary embodiment shown provides a second reference element coupling mechanism 39 that retracts the sample take-up unit 60 somewhat after the puncturing motion and advances it again after the pivoting motion such that a drop of blood can be received by the sample reception channel 63.

The second reference element coupling mechanism 39 comprises a bushing 77 from which extends a rigid steering arm 78 with a steering peg serving as steering curve traveler 79 that engages a steering curve 73 of the drive rotor 12 that is formed by a groove-shaped recess. In the exemplary embodiment shown, the steering curve 68 is arranged on a first side (front side) of the drive rotor 12 and the steering curve 73 on its back side. The bushing 77 is arranged around the coupling rod 70 and inside the bushing 65 of the first reference element coupling mechanism 38.

A complete working cycle of the lancet device shown in FIGS. 8 and 9 proceeds as follows:

The lancet device is placed against a part of a patient's body such that the contact surface 15 of the reference element 14 that is formed by the sample take-up unit 16 rests against the surface of the skin. In order to tension the drive spring 11, the tensioning rotor 13 is rotated by 180°, while the drive rotor 12 is locked by a locking element (not shown). In order to trigger the puncture, the locking element (not shown) is released such that the drive rotor 12 performs a 180° snapping motion until the stop peg 53 hits against the end of the stop groove 52 of the tensioning rotor 53.

During this motion of the drive rotor 12, the crank pin travels along the lower half of a circular path such that the puncturing motion of the lancet 4 is performed by means of the connecting rod 71 and coupling rod 70 of the lancet coupling mechanism 24. During the last section of the snapping motion of the drive rotor 12 the second reference element coupling mechanism 39 causes, by means of the steering curve 73, a retraction of the bushing 77 and the sample take-up unit 60 held therein. Since the contact surface 15 now no longer rests against the surface of the skin, blood can exit.

Subsequently, the tensioning rotor 13 is rotated again by 180° by the motor 40, the drive rotor 12 following this 180°-motion due to the pre-tensioning of the drive spring 11. Due to the shape of the steering curve 68, this leads to a pivoting motion of the bushing 65, the motion being dimensioned such that the orifice 63a (FIG. 10) of the sample take-up unit 60 is directed towards the puncturing site. In the process, the groove 73 causes the sample take-up unit 60 to be advanced again by means of the connecting rod 71 and the coupling rod 70 such that the orifice 63a contacts and aspirates exiting blood.

In place of the crank pin 72 and the connecting rod 71, a third groove in the drive rotor can be used to drive the coupling rod 70 by means of a third steering curve traveler.

In addition, in order to improve the exiting of blood, a pressure piece, for example the lower edge of the bushing 77, can be made to act on the surface of the skin in the vicinity of the puncturing site. By the pressing action of such a pressure piece, blood can be squeezed from the puncture wound to be received by the sample take-up unit 60. The puncture wound closes when the pressure is reduced after the completion of blood withdrawal. Further details regarding the support of blood withdrawal by a pressure piece are disclosed in European patent application EP 04008691.0, which hereby is incorporated into the present application in this respect by way of reference.

In addition, the sample take-up unit 60 is provided with a pump piston 76 (FIG. 10) in order to support the capillary forces of the sample reception channel 63 by means of suction. The sample take-up unit 60 is provided with struts 80 that relax after completed puncture and retract the pump piston 76 such that blood is aspirated into the sample reception channel 63.

A pumping motion in support of the blood withdrawal can also be provided by a suitable design of the steering curves 68 and 73 and/or coupling mechanisms 38, 39, for example by moving tensioning rotor 13 and drive rotor 12 forward and backward over a small range of angles. If the pre-tension of the drive spring 11 is sufficiently strong to ensure essentially synchronous motion of the tensioning rotor 12 and the drive rotor 13, in particular with a relative deviation of their rotation angle by no more than 10°, not only forward motions, but also backward motions are possible with precise steering of the motion.

Figure 11:
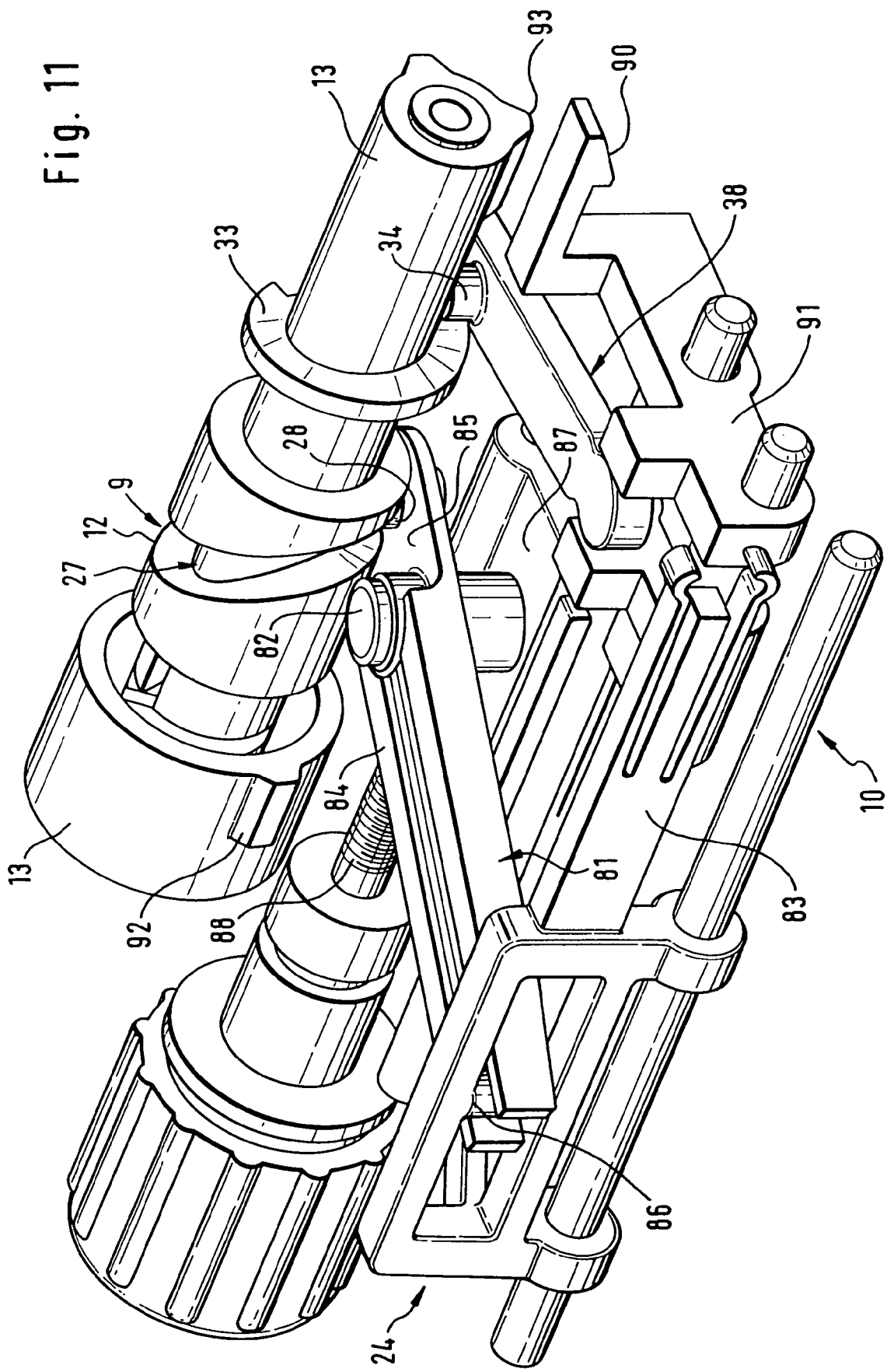
FIG. 11 shows a partial perspective view of a further exemplary embodiment of a lancet drive assembly.

FIG. 11 shows a perspective partial view of a further exemplary embodiment of a lancet drive assembly 10 with a drive rotor 12 and a tensioning rotor 13. For the purpose of simplification, the drive spring is not shown in FIG. 11. The particularity of the assembly 10 shown is a lancet coupling mechanism 24 that comprises a lever 81 to which the steering curve traveler 28 is attached, which traveler travels along the steering curve 27 of the drive rotor 12 that is provided in the form of a groove. The lever 81 is borne on bearings in a pivot 82 to allow a pivoting motion whereby the distance traveled by the lancet holder 83 is larger than the axial stroke of the corresponding flank of the steering curve 27 due to leverage.

The sections 84, 85 of the lever 81 on either side of the pivot 82 each form a lever arm such that the travel enlargement thus achieved corresponds to the ratio of the lengths of the two lever arms 84, 85. These lengths are each to be measured from the pivot 82 outwards, i.e. up to the steering curve traveler 28 and/or attachment point 86 of the lancet holder 83 that is moved by the lever 81.

The leverage described above allows a large travel to be achieved with a small rotor 12, thus with a smaller and more compact device. According to the prior art, a large travel can be achieved solely by a relatively large diameter of the corresponding steering curve 27. Otherwise there would be a risk of self-locking, i.e. a status in which the steering curve traveler 28 locks up and cannot be put into motion again even by a torque of any magnitude. This occurs if the angle of inclination of a steering curve 27 exceeds a critical value, which is a function of the coefficient of friction. However, the described leverage allows a large travel to be achieved even in the case of less inclined flanks of the steering curve 27.

In the embodiment shown, the leverage is part of the lancet coupling mechanism 24 such that the puncturing depth can be adjusted by shifting the pivot 82. However, the advantages of the leverage can also be utilized for other coupling mechanisms that may be coupled to the drive rotor or the tensioning rotor.

In the embodiment shown, the pivot 82 is provided in the form of a peg on a base 87 that can be shifted. The base 87 can be shifted by means of a threaded spindle 88 to allow the puncturing depth to be set. Instead of the threaded spindle 88, for example an eccentric or a wedge can also be used for setting the position of the pivot 82.

In the embodiment shown, the tensioning rotor 13 is so designed that it extends through the drive rotor 12. The tensioning rotor 13 carries a steering curve 33 along which a steering curve traveler 34 of the reference element coupling mechanism 38 travels. When the tensioning rotor 13 is rotated in order to tension the drive spring (not shown), the reference element coupling mechanism 38 advances a reference element carrier 91. The reference element carrier 91 has a snap-in mechanism 90 in the form of a snap-in hook which snaps-in with the housing (not shown) in the process. By this means, the reference element is fixed relative to the lancet drive 9 and relative to the housing (not shown) for the purpose of a puncture.

Since the reference element is pressed against the skin during a puncture, pressure forces act on it, which, by this means, can be borne by the housing via the snap-in mechanism 90. This is advantageous in that the curve steerings 27, 33 of the lancet drive 9 are not exposed to pressure forces, whereby the friction is minimized.

When the tensioning rotor 13 is subsequently rotated even further, a triggering cam 92 that is attached to the tensioning rotor 13 triggers a puncture. The corresponding triggering mechanism can be designed as in the embodiment illustrated on the basis of FIGS. 1 to 5. It is therefore not shown in FIG. 11 for reasons of simplification.

The tensioning rotor 13 carries a further triggering cam 93 that is used in conjunction with a suitable mechanism (not shown) to release the snap-in hook that forms the snap-in mechanism 90 such that the reference element carrier 91, and thus the reference element, can be retracted after a puncture.

LIST OF REFERENCE NUMBERS

1 Lancet device
2 Housing
3 Housing opening
4 Lancet
5 Triggering button
6 Contact surface
7 Edge
8 Finger receptacle
10 Lancet drive assembly
11 Drive spring
12 Drive rotor
13 Tensioning rotor
14 Reference element
15 Contact surface
16 Drum cartridge
17 Protective cap
18 Lancet opening 19 Shaft
20 Exit opening
21 Toothed wheel
22 Toothed rim
24 Lancet coupling mechanism
25 Pushing cylinder
26 Coupling rod (connecting arm)
27 Steering curve
28 Steering curve traveler
29 Steering arm
32 Guiding elements
33 Steering curve
34 Steering curve traveler
35 Coupling arm
36 Guiding rod
37 Gear
38 Reference element coupling mechanism
39 Reference element coupling mechanism
40 Electrical motor
41 Locking element
44 Triggering cam
45 Triggering mechanism
46 Bearing peg
47 Head part
48 Returning surface
49 Head of coupling rod
50 Head
51 Stop parts
52 Stop groove
53 Stop peg
59 Axis
60 Sample take-up unit
61 Guiding channel
63 Sample reception channel
63a Orifice
64 Reaction zone
65 Bushing
66 Steering arm
67 Steering curve traveler
68 Steering curve
69 Bearing peg
70 Coupling rod
71 Connecting rod
72 Crank pin
73 Steering curve
75 Bore hole
76 Pump piston
77 Bushing
78 Steering arm
79 Steering curve traveler
80 Strut
81 Lever
82 Pivot
83 Lancet holder
84, 85 Lever arms
86 Attachment point of the lancet holder
87 Shiftable base
88 Threaded spindle
90 Snap-in mechanism
91 Reference element carrier
92 Triggering cam
93 Cam

What is claimed is:

1. A lancing device, comprising:
    a housing;
    a lancet drive disposed in the housing and including a drive rotor driven by a drive spring;
    a first coupling mechanism disposed in the housing and including a lancet connecting arm configured to connect to a lancet, the first coupling mechanism transforming motion of the drive rotor into reciprocating motion of the lancet connecting arm;
    a reference element that is moveable relative to the housing and relative to the lancet connecting arm, the reference element having a contact surface adapted to contact skin to be punctured during the reciprocating motion of the lancet connecting arm; and
    a second coupling mechanism which couples the reference element to the lancet drive, wherein movement of the lancet drive is transformed into movement of the reference element, the second coupling mechanism transforming movement of the drive rotor into a return movement of the reference element.

2. The lancing device of claim 1, wherein the lancet drive comprises a tensioning rotor for tensioning the drive spring.

3. The lancing device of claim 2, wherein, in a working cycle, the drive rotor runs through a total range of rotation that comprises a preparatory range of rotation during which the drive rotor rotates jointly with the tensioning rotor.

4. The lancing device of claim 3, wherein the reference element is moved by the second coupling mechanism while the drive rotor rotates through the preparatory range of rotation.

5. The lancing device of claim 1, wherein the first coupling mechanism comprises a steering curve along which a steering curve traveler travels in order to transform rotational motion of the drive rotor into the reciprocating motion of the lancet connecting arm.

6. The lancing device of claim 5, wherein the second coupling mechanism comprises a second steering curve along which a second steering curve traveler travels.

7. The lancing device of claim 2, wherein the tensioning rotor comprises a triggering cam that actuates a trigger mechanism when the tensioning rotor is rotated beyond a predetermined angle, whereupon the trigger mechanism releases the drive rotor to start the reciprocating motion of the lancet connecting arm.

8. The lancing device of claim 1, wherein the reference element comprises a pressure sensor that generates a signal for starting a puncturing motion once a pressure in excess of a predetermined minimal pressure is applied to the contact surface.

9. The lancing device of claim 1, wherein the second coupling mechanism transforms a rotational motion of the drive rotor into motion of the reference element.

10. The lancing device of claim 2, wherein the second coupling mechanism transforms rotational motion of the tensioning rotor into motion of the reference element.

11. The lancing device of claim 1, wherein the reference element is arranged in the housing behind a plane that extends through an inner rim that defines an opening in the housing, the inner rim defining a surface that is adapted to press against a body part from which a sample is to be withdrawn.

12. The lancing device of claim 1, wherein the reference element includes a cartridge in which a plurality of lancets can be stored.

13. The lancing device of claim 1, further comprising a sample take-up unit.

14. The lancing device of claim 1, further comprising a locking mechanism configured to fix the reference element relative to the housing.

15. The lancing device of claim 2, wherein the second coupling mechanism couples the reference element to the tensioning rotor for setting a puncturing depth prior to the start of a puncturing motion and couples the reference element to the drive rotor for removing the reference element from the puncturing wound after a puncture.

* * * * *